(12) United States Patent
Mercado et al.

(10) Patent No.: US 8,003,120 B2
(45) Date of Patent: Aug. 23, 2011

(54) POWDER MAKEUP COMPOSITIONS AND METHODS

(75) Inventors: Clara G. Mercado, Saddle River, NJ (US); John F. Logalbo, Dix Hills, NY (US); Khanh Ngoc Dao, Ronkonkoma, NY (US)

(73) Assignee: ELC Management LLC, New York, NY (US)

( * ) Notice: Subject to any disclaimer, the term of this patent is extended or adjusted under 35 U.S.C. 154(b) by 103 days.

(21) Appl. No.: 12/255,975

(22) Filed: Oct. 22, 2008

(65) Prior Publication Data

US 2010/0098765 A1    Apr. 22, 2010

(51) Int. Cl.
*A61K 36/575* (2006.01)
*A61K 36/00* (2006.01)

(52) U.S. Cl. .................................. 424/401; 424/475

(58) Field of Classification Search .................. None
See application file for complete search history.

(56) References Cited

U.S. PATENT DOCUMENTS

| 6,846,846 | B2 * | 1/2005 | Modak et al. ................ 514/722 |
| RE39,218 | E | 8/2006 | Mellul et al. |
| 7,744,932 | B2 * | 6/2010 | Faller et al. .................. 424/725 |
| 2002/0141957 | A1 | 10/2002 | Tan et al. |
| 2002/0157574 | A1 | 10/2002 | Weitzel et al. |
| 2004/0123778 | A1 | 7/2004 | Bagala, Sr. |
| 2005/0033251 | A1 * | 2/2005 | Toreki et al. ................ 604/367 |
| 2005/0142084 | A1 * | 6/2005 | Ganguly et al. ............... 424/63 |
| 2005/0220741 | A1 | 10/2005 | Dumousseaux |
| 2006/0018867 | A1 * | 1/2006 | Kawasaki et al. ........ 424/70.122 |
| 2006/0153889 | A1 * | 7/2006 | Friel et al. ..................... 424/63 |
| 2010/0055139 | A1 * | 3/2010 | Lee ............................. 424/401 |

OTHER PUBLICATIONS

Rosacea Treatment Clinic Online: Mimosa Tenuiflora; URL< http://www.rosacea-treatment-clinic.com.au/Glossaries/Skincare-Ingredients/Mimosa-Tenuiflora.html, accessed Jun. 17, 2010, pp. 1-3.*
Sephora: Clinique Redness Soulutions Instant Relief Mineral Powder; Online, URL<http://answers.sephora.com/answers/8723/product/P232339/questions.htm>, accessed Jun. 18, 2010, pp. 1-5.*
PCT International Search Report; International Application No. PCT/US2009/055002, Completion Date: Mar. 23, 2010; Date of Mailing: Mar. 24, 2010.
PCT Written Opinion of the International Searching Authority, Or the Declaration; International Application No. PCT/US2009/05002; Completion Date: Mar. 23, 2010; Mailing Date: Mar. 24, 2010.
http://www.gnpd.com; Maple Powder Foundation; Record ID: 579831; Von Natur; Von Natur; Colour Cosmetics; Face Colour Cosmetics—Foundations / Fluid Illuminators; USA; Aug. 25, 2006.
http://www.gnpd.com; Pressed Powder UV; Record ID: 355561; Sana: Natural Resource; Colour Cosmetics; Face Colour Cosmetics—Foundations / Fluid Illuminators; Japan; Apr. 21, 2005.

(Continued)

*Primary Examiner* — Patricia Leith
(74) *Attorney, Agent, or Firm* — Julie Blackburn

(57) ABSTRACT

An anhydrous powder composition wherein the ratio of platelet to non-platelet particulates is greater than about 5 to 1 respectively, which is preferably talc-free, oil-free, paraben-free, and fragrance-free; and a method for preparing the powder composition of the invention.

35 Claims, 1 Drawing Sheet

Line 1: Anhydrous Powder – Treated with Ultra Rotor
Line 2: Anhydrous Powder – Treated with Pulverizer

OTHER PUBLICATIONS http://www.gnpd.com; Face Up Powder N; Record ID: 824500; Kanebo Cosmetics; Free Plus; Colour Cosmetics; Face Colour Cosmetics—Powder; Japan; Dec. 4, 2007.

http://www.gnpd.com; Powder Foundation (04); Record ID: 355562; Sana; Natural Resource; Colour Cosmetics; Face Colour Cosmetics—Foundations / Fluid Illuminators; Japan; Apr. 21, 2005.

http://www.gnpd.com; Mineral Double Compact; Record ID: 906693; Sephora; Sephora; Colour Cosmetics; Face Colour Cosmetics—Foundations / Fluid Illuminators; Spain; May 7, 2008.

http://www.gnpd.com; Mineral Makeup SPF 15; Record ID: 959124; BeautiControl; BeautiControl Secret Agent; Colour Cosmetics; Face Colour Cosmetics—Foundations / Fluid Illuminators; USA; Aug. 18, 2008.

http://www.gnpd.com/sinatra/gnpd/search_results/&item_id=956762; Transparent Finish To Go Brush & Powder; Alison Raffaele Cosmetics; Alison Raffaele; UK; Aug. 2008.

http://www.gnpd.com/sinatra/gnpd/search_results/&item_id=961362; Lotion-to Powder; Susan Brown's Baby; Susan Brown's Baby Sensitive Baby; USA; Aug. 2008.

http://www.gnpd.com/sinatra/gnpd/search_results/&item_id=982252; Eyeshadow Quad; Avon; Avon True Color Summer Bronze; Brazil; Oct. 2008.

http://www.gnpd.com/sinatra/gnpd/search_results/&item_id=976837; Make Up Pressed Powder; Kanebo Cosmetics; Coffret D'Or; Japan; Sep. 2008.

* cited by examiner

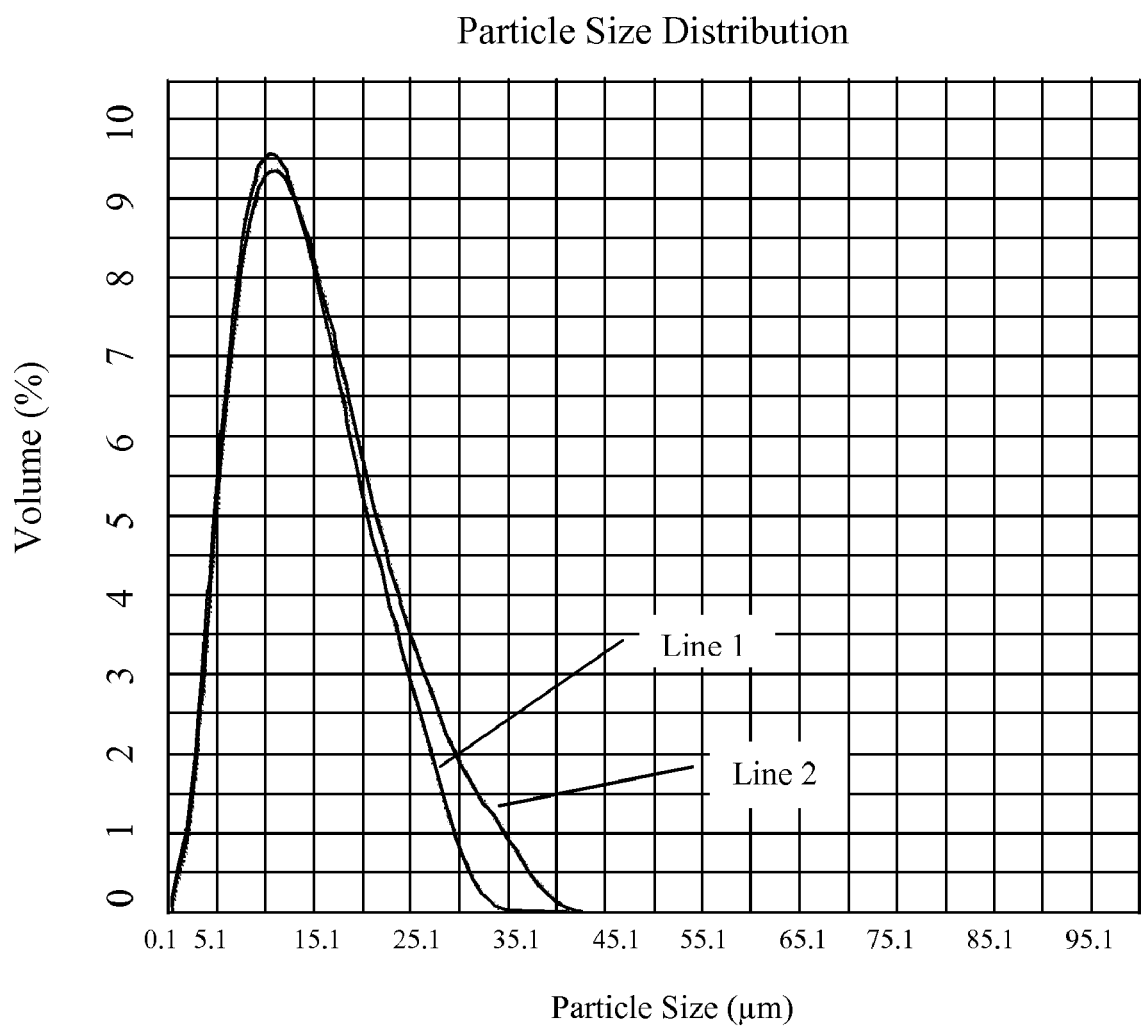
Line 1: Anhydrous Powder – Treated with Ultra Rotor
Line 2: Anhydrous Powder – Treated with Pulverizer

POWDER MAKEUP COMPOSITIONS AND METHODS

TECHNICAL FIELD

The invention is in the field of color cosmetic compositions for application to skin or lips.

BACKGROUND OF THE INVENTION

Women wear color cosmetics such as foundation for a variety of reasons including a desire to even skin tone, cover blemishes and other skin imperfections, or provide a more aesthetic and flawless finish. While color cosmetics such as foundations and powders with these benefits are commercially available, often there is a trade off between coverage and natural appearance on the skin. For example, foundations that exhibit the most coverage tend to be very opaque. Such opacity is visible on the face. In fact, such visibility is most noticeable during the day time in bright sunlight or with high definition television. When makeup appears visible on the face it is generally perceived to gather in lines and wrinkles or on facial depressions like lip lines or on the sides of the nose. Thus, the gold standard for foundations and powders is to provide maximum coverage yet appear natural, as though the user was wearing nothing and had beautiful skin.

It has been discovered that providing particulates used in foundations, powders, and other color cosmetics for application to skin and lips in a substantially platelet form maximizes coverage and provides the most naturally appearing finish on the skin.

It is an object of the invention to provide a color cosmetic composition comprising particulates wherein the particulates are in substantially platelet form.

It is a further object of the invention to provide an anhydrous powder composition comprising platelet and non-platelet particulates wherein the ratio of the platelet to non-platelet particulates is greater than 5 to 1 respectively.

It is a further object of the invention to provide an anhydrous powder composition where the particulates present are substantially in the platelet form and wherein the composition is substantially free of talc, parabens, oil, and fragrances.

It is a further object of the invention to provide a method for reducing the appearance of skin redness by applying a composition comprising platelet and non-platelet particulates wherein the ratio of platelet to non-platelet particulates is greater than about 5 to 1 respectively.

It is a further object of the invention to provide a method for improving uneven pigmentation, the appearance of blemishes or skin imperfections by applying a composition comprising particulates where the particulates are substantially in the form of platelets.

It is a further object of the invention to provide a complex of ingredients that, when used to treat powder particles, provides a skin soothing effect that ameliorates the appearance of skin redness.

SUMMARY OF THE INVENTION

The invention is directed to an anhydrous powder composition comprising platelet and non-platelet particulates wherein the ratio of platelet to non-platelet particulates is greater than about 5 to 1 respectively.

The invention is further directed to a method for preparing powder compositions containing a skin treatment active comprising the steps of:

treating the particulates with the skin treatment active prior to incorporation into the powder formula; and normalizing the particulates.

It is a further object to provide a method for reducing the appearance of skin redness by applying a composition comprising platelet and non-platelet particulates wherein the ratio of the platelet to non-platelet particulates is greater than about 5 to 1.

It is a further object of the invention to provide a method for improving the appearance of uneven pigmentation, blemishes or skin imperfections by applying a composition comprising platelet and non-platelet particulates wherein the ratio of platelet to non-platelet particulates is greater than about 5 to 1 respectively.

DESCRIPTION OF THE DRAWINGS

The FIGURE shows the difference in particle size distribution of the anhydrous powder of Example 1 when treated with a pulverizer and when treated according to the method of the invention.

DETAILED DESCRIPTION

I. Definitions

All percentages mentioned herein are percentages by weight unless otherwise indicated.

"Anhydrous" means, with respect to the composition, that no water is intentionally added, but the composition may contain water that is present in amounts generally less than 1% by weight as components of raw materials, for example.

The term "complex" means a mixture of ingredients.

"Fragrance", when used with "substantially free of" means any synthetic organic compound or mixture of compounds that provides aromatic character.

"Non-Platelet" means a particulate that is other than in the Platelet shape, e.g. spherical.

"Normalize" means that the particulates become more uniform in size and shape and generally exhibit a reduced particle size distribution when compared to the particulates prior to treatment. Normalizing of particulates may be performed with different types of equipment normally used in preparation of powders, including but not limited to rotors, containerized batch mixers and the like.

"Oil" means, when used with "substantially free of" means animal derived oils or mineral oil, where such oil is pourable at room temperature (25° C.)

"Paraben", when used with "substantially free of", means methyl, ethyl, propyl, or butyl paraben or combinations thereof "Platelet" means a particulate that is in the plate or disc shape.

"Redness" with respect to skin means that the skin exhibits a reddish color which may be due to rosacea, windburn, sunburn, skin irritation, allergy, broken capillaries, or similar skin conditions that cause the skin to appear reddish.

"Substantially free of" means, with respect to the ingredient referred to, that the ingredient is not intentionally added to the composition but it may be present in trace amounts as components of other raw materials, generally less than 1% by weight.

"Talc", when used with "substantially free of" means naturally occurring or synthetic talc powder.

II. The Composition

A. Particulates

The composition of the invention are in the anhydrous powder form. They contain particulates in amount ranging from about 10 to 99%, preferably from about 15 to 95%, more preferably from about 20 to 90%. The particulates are in the form of platelet particulates and non-platelet particulates. The ratio of platelet to non-platelet particulates in the composition is greater than about 5 to 1; preferably greater than about 6 to 1 respectively. The particulates may vary in size from about 0.001 to 100 microns, preferably from about 0.005 to 50 microns, more preferably from about 0.1 to 40 microns. In another more preferred embodiment, more than about 75% of the total particulates present are normalized to have a particle size distribution within a range of from about 1 to 40 microns.

In preparing the compositions of the invention, suitable platelet particulates may include those that are naturally in the platelet form such as mica, titanated mica, sericite, bismuth oxychloride, bentonite, and the like. Alternatively, the platelet particulates may be particulates that, after treatment in an Ultra Rotor or similar grinding machine become platelet shapes.

The composition also contains non-platelet particulates that may be in the form of spherical or non-spherical particles. Preferably at least some of the non-platelet particulates are in the spherical form. Examples of non-platelet particulates include HDI/trimethylolhexyllactone crosspolymer, silica, fumed silica, spherical silica, boron nitride, PTFE, PMMA, nylon, and so on.

Particulates that may be in platelet or non-platelet form initially include, but are not limited to pigments such as iron oxides in the black, red, or yellow form; organic pigments that are D&C and FD&C pigments and Lakes thereof such as FD&C Yellow #5, D&C Yellow #5, D&C Red #7, and so on, titanium dioxide, or powders such as aluminum silicate, aluminum starch octenylsuccinate, calcium silicate, cellulose, chalk, corn starch, diatomaceous earth, fuller's earth, glyceryl starch, hectorite, kaolin, magnesium aluminum silicate, magnesium trisilicate, maltodextrin, rice starch, titanium dioxide, zinc laurate, zinc myristate, zinc rosinate, alumina, attapulgite, calcium carbonate, calcium silicate, dextran, kaolin, nylon, silica silylate, soy flour, tin oxide, titanium hydroxide, trimagnesium phosphate, walnut shell powder, or mixtures thereof.

The preferred compositions of the invention comprise from about 45-99%, preferably from about 50-95%, more preferably from about 55-85% of platelet particulates and from about 1-55%, preferably from about 1-50%, more preferably from about 1-45% of non-platelet particulates. The preferred compositions comprise from about 0.1-35%, preferably 0.5-30%, more preferably from about 1-25% pigment, and from about 65-99.9%, preferably from about 60-99.5%, more preferably from about 75-99% powder.

B. Skin Treatment Active

The composition preferably contains one or more skin treatment actives. Suggest ranges are from about 0.01-60%, preferably from about 0.05-50%, more preferably from about 1 to 45%. Skin treatment actives include any ingredients that exhibit activity in ameliorating skin conditions such as redness, irritation, acne, blemishes, cuts, scratches, dryness, uneven pigmentation, itchiness, oiliness, and the like. Skin treatment actives may act on the skin in a variety of different ways, such as acting as humectants, emollients, anti-inflammatory ingredients, anti-acne, and the like. Suitable skin treatment actives include, but are not limited to vitamins or vitamin derivatives such as A, B, C, E, D, K; botanical extracts from plants, flowers, trees, or shrubs; caffeine; emollients from plant sources such as plant waxes or butters; and the like. Examples of botanicals include but are not limited to *Poria Cocos* extract, *Magnolia Grandiflora* Bark extract, *Citrus Grandis* Peel extract, *Siegesbeckia Orientalis*, *Rosmarinus Officinalis*, *Mangifera Indicia*, *Hordeum Vulgare*, *Punica Granatum*, *Saccharomyces Cervisiaea*, *Pyrus Malus*, *Cucumis Sativus*, *Scutelleria Baicalensis*, *Camellia Sinensis*, *Chamomile Recutita*, *Helianthus Annus*, *Betula Alba*, *Saccharomyces Lysate*, *Porphyra Yezoensis*, *Salicornia Herbacea*, *Citrus Unshiu*, *Curcuma Longa*, *Schinziophyton Tautanenii* Kernel oil, *Trichilia Emetica*, *Sclerocarya Birrea*, *Polygonum Cuspidatum*, *Humulus Lupulus*, *Selaginella Tamariscina*, *Citri Reticulatae*, *Aloe Barbadensis*, *Punica Granatum*, and the like.

Also suitable as the skin soothing emollients are naturally occurring plant waxes or butters such as *Astrocaryum Murumuru* butter, *Shea* butter, *Acacia Dealbata* flower or seed wax, *Acacia Decurrans* wax, *Persea Gratissima* wax, *Rosa Hybrid* flower wax, *Rosa Multiflora* flower wax, *Theobroma Grandiflora* seed butter, *Astrocaryum Tucuma* seed butter, *Jojoba* butter, *Lavendula Augustifolia* wax, *Myrica Cerefera* wax, Cocoa butter, *Garcinia Indica* seed butter, and the like.

Other types of skin actives include anti-acne actives such as benzoyl peroxide or salicylic acid; anti-inflammatory ingredients such as hydrocortisone; peptides such as acetyl hexapeptide-3, palmitoyl pentapeptide, palmitoyl oligopeptide, etc.; DNA repair enzymes such as OGGI, micrococcus lysate; and so on.

The skin soothing active may be in the form of a complex. In this case the ingredients that provide the skin soothing and redness ameliorating effects are pre-mixed in the appropriate ratio to maximize the redness relief effects. An example of such a complex may include *Poria Cocos* extract, *Magnolia Grandiflora* bark extract, *Astrocaryum Murumuru* butter, caffeine, and optionally minerals, with each ingredient present in the range of about 0.1 to 60% by weight of the total complex composition.

C. Binders

The anhydrous powder composition may contain one or more ingredients that act as a binder to cause the particles to be cohesive. If present, the amount of binder may range from about 0.01 to 50%, preferably from about 0.05 to 40%, more preferably from about 0.1 to 35%. Suitable binders may include natural or synthetic solids, semi-solids, or liquids. Examples of natural or synthetic solids include waxes such as polyethylene, C2-40 straight or branched chain hydrocarbons that may be volatile or non-volatile; C1-4 alkyl esters of C6-30 saturated or unsaturated fatty acids, for example isopropyl palmitate, isopropyl myristate, isopropyl triisostearate; phospholipids such as lecithin; and the like.

D. Preservatives

The anhydrous powder composition may also comprise one or more preservatives. Suggested ranges are from about 0.1 to 20%, preferably from about 0.5 to 15%, more preferably from about 0.5 to 10%. Preservatives include phenoxyethanol, chlorophenesin, and so on.

Preferred compositions of the invention are substantially free of one, preferably all of these ingredients: oil, talc, parabens, and fragrance.

Preferred compositions of the invention are where the particulates present are substantially in platelet form, that is preferably more than about 55% of the particulates present are in the platelet form. Further, such preferred compositions are where more than about 75% of the particulates present have a particle size distribution in the range of from about 1 to 40 microns.

III. The Methods

The invention is directed to a method for preparing powder compositions containing a skin treatment active comprising the steps of:

treating the particulates with the skin treatment active prior to incorporation into the powder formula; and normalizing the particulates.

In the method of the invention the powder particles are preferably sprayed with the active ingredient using a fluid bed granulator, which ensures that the particles are evenly coated with the skin care active. Then the batch is subjected to a rotor spun at high speed for a period of time to normalize the particles such that they exhibit a narrower particle size distribution and may form platelets. If desired the particulates can be subjected to mixing using a containerized batch mixer either before, after, or between the treatment with the fluid bed granulator and the high speed rotor. These treatments provide a powder having a diminished particle size distribution, and where a large percentage of the particulates are in the platelet form.

The invention further provides a method for reducing the appearance of skin redness by applying a composition comprising platelet and non-platelet particulates wherein the ratio of the platelet to non-platelet particulates is greater than about 5 to 1.

The invention is also directed to a method for improving the appearance of uneven pigmentation, blemishes or skin imperfections by applying a composition comprising platelet and non-platelet particulates wherein the ratio of platelet to non-platelet particulates is greater than about 5 to 1 respectively.

In both cases the powder may be applied to the invention one or more times per day. It may be used alone, or applied after application of foundation makeup. It may be used with other color cosmetics.

It has been found that the anhydrous powder of the invention exhibits substantially improved coverage for skin redness and other skin imperfections. The reduced particle size distribution and/or substantially platelet form provides more even coverage without giving a "made up" appearance. Thus, the powder of the invention is excellent for use by consumers who have rosacea or those who have other skin imperfections.

The invention will be further described in connection with the following examples which are set forth for the purposes of illustration only.

EXAMPLE 1

A powder composition was prepared as follows:

| Ingredient | wt % |
| --- | --- |
| Sericite | QS |
| Mica/lauroyl lysine | 26.51 |
| HDI/trimethylol hexyllactone crosspolymer/silica | 6.00 |
| Polyethylene | 10.00 |
| Magnesium myristate | 1.00 |
| Bismuth oxychloride/silica/mica | 3.00 |
| Chlorophenesin | 0.30 |
| Potassium sorbate | 0.20 |
| Tetrasodium EDTA | 0.05 |
| FD&C Yellow No. 5 Aluminum Lake | 0.39 |
| Yellow iron oxides | 0.23 |
| Red iron oxides | 0.01 |
| Black iron oxides | 0.01 |
| Bentonite | 0.50 |
| *Magnolia Grandiflora* bark extract | 0.05 |
| Poria Cocos extract | 0.05 |
| Caffeine | 0.10 |
| *Citrus Grandis* (Grapefruit) peel extract | 0.10 |
| *Astrocaryum Murumuru* seed butter | 0.20 |
| Phytosqualane | 0.01 |
| Isopropyl palmitate | 1.00 |
| Lecithin | 0.10 |
| Tocopheryl acetate | 0.10 |
| Squalane | 0.09 |

The bentonite, *Magnifolia Grandiflora* Bark extract, *Porios Cocos* extract, caffeine, and *Citrus Grandis* Peel extract (Sequence 2) were combined in a containerized batch mixer manufactured by Readco (www.readco.com), Model CBM2040 and mixed at full speed for 2 minutes. The sides of the mixer were scraped and the high speed mixing was repeated for another 2 minutes. After this treatment the mixture was pulverized one time using a 0.020 inch screen. The *Astrocaryum Murumuru* seed butter and phytosqualene (Sequence 3) were combined and heated to 70° C. with prop mixing until the mixture was clear and uniform. The Sequence 2 ingredients were loaded into a Magnaflo® fluid bed granulator sold by Fluid Air, Inc.® and the Sequence 3 ingredients were sprayed into the Sequence 2 ingredients in the granulator. The mica, mica/lauroyl lysine, HDI/trimethylol hexyllactone crosspolymer/silica, polyethylene, magnesium myristate, bismuth oxychloride/silica/mica, chlorophenesin, potassium sorbate, tetrasodium EDTA, FD&C Yellow No. 5 Aluminum Lake, and iron oxides were loaded into the containerized batch mixer. Sequences 2 and 3 were added and the batch was mixed at full speed for 2 minutes. The sides of the mixer were scraped and two additional mixing steps of 2 minutes each at full speed were performed. The temperature of the batch was not allowed to exceed 70° C. The entire batch was passed through a pulverizer once using a 0.010 inch screen, then reweighed and introduced into a clean containerized batch mixer. Separately, the isopropyl palmitate, lecithin, tocopheryl acetate, squalane, and *Astrocaryum Murumuru* Seed butter (Sequence 4) were combined and heated to 70° C. with prop mixing until the mixture was clear and uniform. Aliquots of the Sequence 4 mixture were sprayed into the batch comprised of Sequences 1, 2, and 3 in the containerized batch mixer. The entire batch was then introduced into an Ultra Rotor I, Altenburger Maschinen Jackering GmbH, having a drive of 7.5/11/15 kW, a size of 1400×1000×920 mm; a capacity of 10-100 kg/h; and an evaporation capacity of 10-25 kg/h and spun at 6,000 rpm 40 kg/hr feed rate, ensuring that the temperature did not exceed 70° C. for 3 minutes. The powder was stored in compacts.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A powder composition comprising platelet and non-platelet particulates, wherein the composition comprises from about 55-85% of platelet particulates and from about 1-45% of non-platelet particulates and the ratio of platelet to non-platelet particulates is greater than 5 to 1 respectively, the composition comprises less than 1% water, more than 75% of the platelet and non-platelet particulates have a particle size of from about 0.1 to about 40 microns, and wherein the platelet particulates comprise bentonite and the platelet and non-platelet particulates comprise a skin treatment active comprising *Poria cocos* extract, *Magnolia grandiflora* bark extract, *Astrocaryum murumuru* butter and caffeine.

2. The composition of claim 1 wherein the ratio of platelet to non-platelet particulates is greater than about 6 to 1.

3. The composition of claim 1 wherein the ratio of platelet to non-platelet particulates is from greater than about 5 to 1 to about 6 to 1.

4. The composition of claim 1 which is substantially free of talc.

5. The composition of claim 1 which is substantially free of oil.

6. The composition of claim 1 which is substantially free of parabens.

7. The composition of claim 1 which is substantially free of fragrance.

8. The composition of claim 1 wherein the platelet particulates further comprise mica, bismuth oxychloride, sericite, or mixtures thereof.

9. The composition of claim 1 wherein the composition is prepared by a process comprising coating platelet and non-platelet particulates with the skin treatment active; and spinning the coated particulates for a period of time such that more than 75% of the particulates have a particle size of from about 0.1 to about 40 microns.

10. The composition of claim 9 wherein, the process further comprises, granulating the coated particulates prior to spinning.

11. The composition of claim 10 wherein the granulating is performed in a fluid-bed granulator.

12. The composition of claim 9, wherein the composition is prepared by a process further comprising spinning the coated particulates for a period of time such that the composition comprises from about 55-85% of platelet particulates and from about 1-45% of non-platelet particulates and that the ratio of platelet to non-platelet particulates is greater than 5 to 1.

13. The composition of claim 1 wherein the non-platelet particulates further comprise polyethylene.

14. The composition of claim 13 wherein the non-platelet particulates further comprise HDI/trimethylol hexyllactone crosspolymer.

15. The composition of claim 1 further comprising a binder which is a C1-4 alkyl ester of a C6-30 saturated or unsaturated fatty acid.

16. The composition of claim 15 wherein the binder comprises isopropyl palmitate.

17. The composition of claim 1 wherein the skin treatment active further comprises *Citrus grandis* peel extract.

18. The composition of claim 1, wherein more than about 75% of the particulates have a particle size of from 1 to about 40 microns.

19. A powder composition prepared by a process comprising:

coating platelet and non-platelet particulates with *Poria cocos* extract, *Magnolia grandiflora* bark extract, *Astrocaryum murumuru* butter and caffeine, wherein the platelet particulates comprise bentonite; and spinning the coated particulates for a period of time such that more than 75% of the particulates have a particle size of from about 0.1 to about 40 microns, wherein the composition comprises less than 1% water.

20. The composition of claim 19 wherein the process comprises spinning the coated particulates for a period of time such that more than 75% of the particulates have a particle size of from about 1 to about 40 microns.

21. The composition of claim 19 wherein the process further comprises spinning the coated particulates for a period of time such that the composition comprises from about 55-85% of platelet particulates and from about 1-45% of non-platelet particulates and that the ratio of platelet to non-platelet particulates is greater than 5 to 1.

22. The composition of claim 19 wherein the ratio of platelet to non-platelet particulates is greater than about 6 to 1.

23. The composition of claim 19 wherein the ratio of platelet to non-platelet particulates is from greater than 5 to 1 to about 6 to 1.

24. The composition of claim 19 which is substantially free of talc.

25. The composition of claim 19 which is substantially free of oil.

26. The composition of claim 19 which is substantially free of parabens.

27. The composition of claim 19 which is substantially free of fragrance.

28. The composition of claim 19 wherein the platelet particulates further comprise mica, bismuth oxychloride, sericite, or mixtures thereof.

29. The composition of claim 19 wherein the process further comprises granulating the coated particulates prior to spinning.

30. The composition of claim 29 wherein the granulating is performed in a fluid-bed granulator.

31. The composition of claim 19 wherein the non-platelet particulates further comprise polyethylene.

32. The composition of claim 31 wherein the non-platelet particulates further comprise HDI/trimethylol hexyllactone crosspolymer.

33. The composition of claim 19 further comprising a binder which is a C1-4 alkyl ester of a C6-30 saturated or unsaturated fatty acid.

34. The composition of claim 33 wherein the binder comprises isopropyl palmitate.

35. The composition of claim 19 wherein the process further comprises coating the platelet and non-platelet particulates with *Citrus grandis* peel extract.

* * * * *